United States Patent [19]
Shimada et al.

[11] Patent Number: 5,356,742
[45] Date of Patent: Oct. 18, 1994

[54] DIPYRENYLAMINE DERIVATIVES AND ELECTROPHOTOGRAPHIC PHOTOCONDUCTOR COMPRISING THE SAME

[75] Inventors: Tomoyuki Shimada, Shizuoka; Masaomi Sasaki, Susono; Tamotsu Aruga, Mishima; Hiroshi Adachi, Numazu, all of Japan

[73] Assignee: Ricoh Company, Ltd., Tokyo, Japan

[21] Appl. No.: 842,993

[22] Filed: Feb. 28, 1992

[30] Foreign Application Priority Data

Mar. 1, 1991 [JP] Japan .................. 3-059475
Jul. 9, 1991 [JP] Japan .................. 3-195880

[51] Int. Cl.$^5$ .................. G03G 5/047; G03G 5/09
[52] U.S. Cl. .................. 430/59; 430/73; 430/74; 430/75; 430/76; 430/77; 430/78; 430/79; 430/83
[58] Field of Search .................. 430/59, 73, 74, 75, 430/76, 77, 78, 79, 83

[56] References Cited

U.S. PATENT DOCUMENTS

| | | | |
|---|---|---|---|
| 3,307,940 | 3/1967 | Hoegl et al. | 430/73 X |
| 4,233,384 | 11/1980 | Turner et al. | 430/59 |
| 5,079,118 | 1/1992 | Kikuchi et al. | 430/75 X |
| 5,219,692 | 6/1993 | Shimada et al. | 430/59 |

FOREIGN PATENT DOCUMENTS

| | | | |
|---|---|---|---|
| 51163 | 2/1990 | Japan | 430/59 |
| 190863 | 7/1990 | Japan | 430/59 |
| 63653 | 3/1991 | Japan | 430/74 |

*Primary Examiner*—Roland Martin
*Attorney, Agent, or Firm*—Oblon, Spivak, McClelland, Maier & Neustadt

[57] ABSTRACT

An electrophotographic photoconductor is composed of an electroconductive substrate and a photoconductive layer formed thereon, the photoconductive layer includes a dipyrenylamine derivative of formula (I):

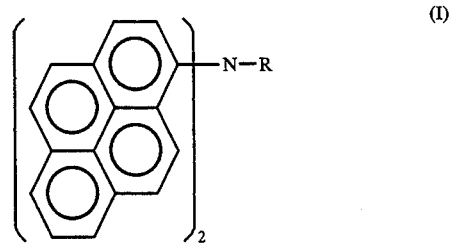

wherein R represents an alkyl group with 1 to 12 carbon atoms, which may have a substituent, or an aryl group which may have a substituent. Novel dipyrenylamine derivatives of formula (I), in which R is —ph—(R$^4$)n, wherein, ph is a phenyl group, R$^4$ is hydrogen, an unsubstituted or substituted alkyl group having 1 to 12 carbon atoms, an unsubstituted or substituted alkoxyl group having 1 to 12 carbon atoms, n is an integer of 1 to 5, and when n is 2 to 5, R$^4$ may be the same or different, which are for use in the photoconductive layer of the electrophotographic photoconductor, are synthesized.

42 Claims, 4 Drawing Sheets

DIPYRENYLAMINE DERIVATIVES AND ELECTROPHOTOGRAPHIC PHOTOCONDUCTOR COMPRISING THE SAME

BACKGROUND OF THE INVENTION

1. Field of the Invention

The present invention relates to dipyrenylamine derivatives, methods of synthesizing the dipyrenylamine derivatives, and an electrophotographic photoconductor comprising a photoconductive layer comprising at least one dipyrenylamine derivative overlaid on an electroconductive substrate.

2. Discussion of Background

Conventionally, inorganic materials such as selenium, cadmium sulfide and zinc oxide are used as a photoconductive material of an electrophotographic photoconductor in the electrophotographic process. The above-mentioned electrophotographic process is one of the image forming processes, through which the surface of the photoconductor is charged uniformly in the dark to a predetermined polarity, for instance, by corona charge. The uniformly charged photoconductor is exposed to a light image to selectively dissipate the electrical charge of the exposed areas, so that a latent electrostatic image is formed on the photoconductor. The thus formed latent electrostatic image is developed by a developer comprising a coloring agent such as a dye and a pigment, and a binder agent such as a polymeric material, to a visible image.

Fundamental characteristics required for the photoconductor for use in such an electrophotographic process are: (1) chargeability to an appropriate potential in the dark, (2) minimum dissipation of electrical charge in the dark, and (3) rapid dissipation of electrical charge when exposed to light.

However, while the above-mentioned inorganic materials have many advantages, they have several shortcomings from the viewpoint of practical use.

For instance, a selenium photoconductor, which is widely used at present, satisfies the above-mentioned requirements (1) to (3) completely, but it has the shortcomings that its manufacturing conditions are difficult and, accordingly, its production cost is high. In addition, it is difficult to work it into the form of a belt due to its poor flexibility, and it is so vulnerable to heat and mechanical shocks that it must be handled with the utmost care.

A cadmium sulfide photoconductor and a zinc oxide photoconductor can be easily obtained by coating a dispersion of cadmium sulfide particles and zinc oxide particles respectively in a binder resin on a substrate. However, they are poor in mechanical properties, such as surface smoothness, hardness, tensile strength and wear resistance. Therefore, they cannot be used in the repeated operation.

To solve the problems of the inorganic materials, various electrophotographic photoconductors employing organic materials have been proposed recently and some are put to practical use. For example, there are known a photoconductor comprising poly-N-vinylcarbazole and 2,4,7-trinitrofluorene-9-on, as disclosed in U.S. Pat. No. 3,484,237; a photoconductor prepared by sensitizing poly-N-vinylcarbazole with a pigment of pyrylium salt, as described in Japanese Patent Publication 48-25658; a photoconductor comprising as the main component an organic pigment, as described in Japanese Laid-Open Patent Application 47-37543; a photoconductor comprising as the main component an eutectic crystal complex of a dye and a resin, as described in Japanese Laid-Open Patent Application 47-10735; a photoconductor prepared by sensitizing a triphenylamine compound with a sensitizer pigment, as described in U.S. Pat. No. 3,180,730; a photoconductor comprising an amine derivative as a charge transporting material, as described in Japanese Laid-Open Patent Application 57-195254; a photoconductor comprising poly-N-vinylcarbazole and an amine derivative as charge transporting materials, as described in Japanese Laid-Open Patent Application 58-1155; and a photoconductor comprising a polyfunctional tertiary amine compound, in particular benzidine compound, as a photoconductive material, as described in U.S. Pat. No. 3,265,496, Japanese Patent Publication 39-11546 and Japanese Laid-Open Patent Application 53-27033.

These electrophotographic photoconductors have their own excellent characteristics and considered to be valuable for practical use. With various requirements of the electrophotographic photoconductor in electrophotography taken into consideration, however, the above-mentioned conventional electrophotographic photoconductors cannot meet all the requirements for use in electrophotography.

SUMMARY OF THE INVENTION

It is therefore a first object of the present invention to provide an electrophotographic photoconductor free from the conventional shortcomings, which can completely satisfy all the requirements in the electrophotographic process, including high durability, and can be easily manufactured at relatively low cost.

A second object of the present invention is to provide novel dipyrenylamine derivatives serving as photoconductive materials for use in the above-mentioned electrophotographic photoconductor.

A third object of the present invention is to provide methods of preparing the above novel dipyrenylamine derivatives.

The first object of the present invention can be achieved by an electrophotographic photoconductor comprising an electroconductive substrate and a photoconductive layer formed thereon, which comprises a dipyrenylamine derivative of formula (I):

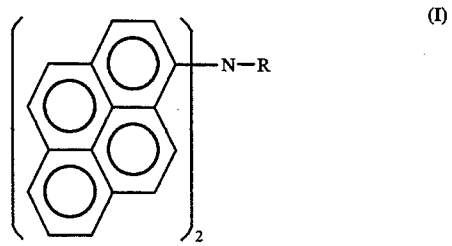

wherein R represents an alkyl group with 1 to 12 carbon atoms, which may have a substituent, or an aryl group which may have a substituent.

The second object of the present invention can be achieved by a dipyrenylamine derivative having formula (II):

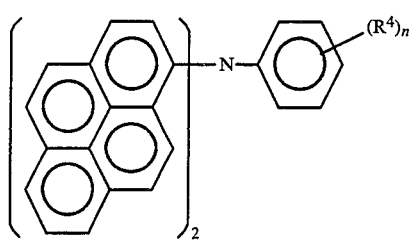
(II)

wherein $R^4$ represents hydrogen, an alkyl group having 1 to 12 carbon atoms, which may have a substituent, an alkoxyl group represented by —$OR^1$, in which $R^1$ represents an alkyl group having 1 to 12 carbon atoms, which may have a substituent, a phenyl group which may have a substituent, or a halogen; n is an integer of 1 to 5; and when n is 2 to 5, $R^4$ may be the same or different.

The third object of the present invention can be attained by a method of preparing a dipyrenylamine derivative having the above formula (II) comprising the step of allowing an aniline derivative having formula (III) to react with a halogenopyrene having formula (IV):

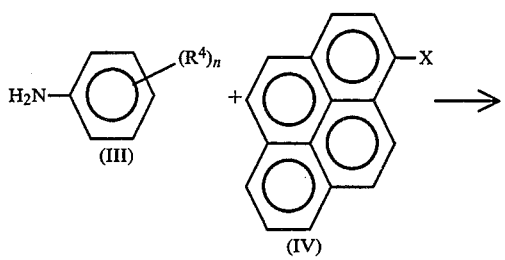
(III)             (IV)

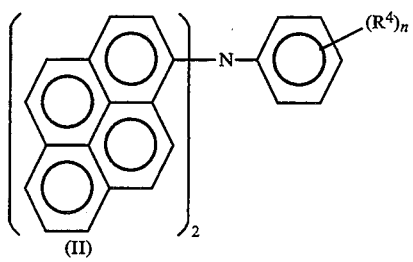
(II)

wherein $R^4$ and n are the same as defined in the formula (II); and X represents a halogen.

The third object of the present invention can also be attained by a method of preparing a dipyrenylamine derivative of the formula (II) comprising the step of allowing a N-phenyl-1-aminopyrene derivative having formula (V) to react with a halogenopyrene having formula (IV):

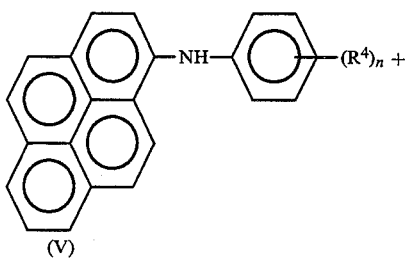
(V)

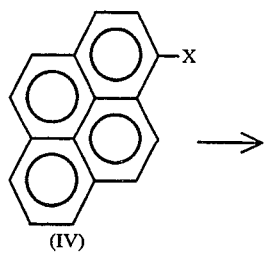
(IV)

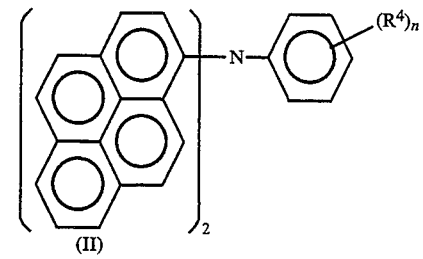
(II)

wherein $R^4$ and n are the same as defined in the formula (II); and X represents a halogen.

BRIEF DESCRIPTION OF THE DRAWINGS

A more complete appreciation of the invention and many of the attendant advantages thereof will be readily obtained as the same becomes better understood by reference to the following detailed description when considered in connection with the accompanying drawings, wherein.

DETAILED DESCRIPTION OF THE PREFERRED EMBODIMENTS

Figure 1:
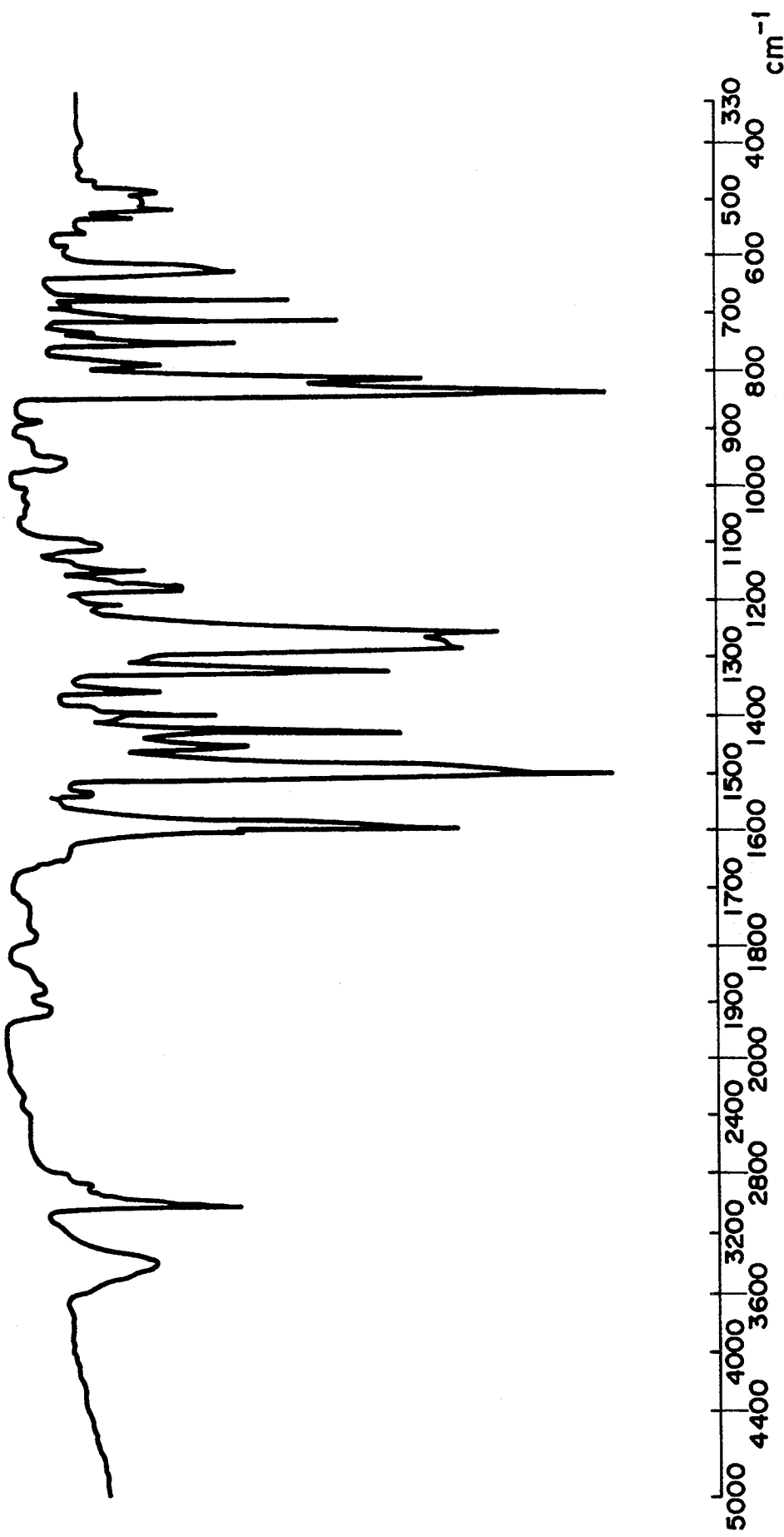
FIG. 1 is an IR spectrum of a dipyrenylamine derivative obtained in Preparation Example 1.

An electrophotographic photoconductor according to the present invention comprises an electroconductive substrate and a photoconductive layer formed thereon, comprising at least one dipyrenylamine derivative of formula (I):

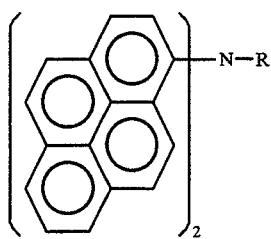

(I)

wherein R represents an alkyl group which may have a substituent, or an aryl group which may have a substituent.

The dipyrenylamine derivative of the above-mentioned formula (I) can be prepared by allowing a halogenopyrene having formula (IV) to react with an amine derivative having formula (IIIa):

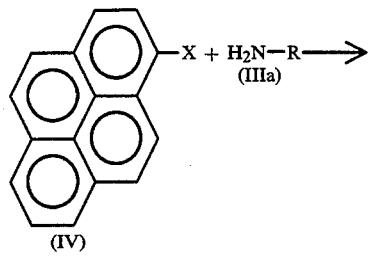

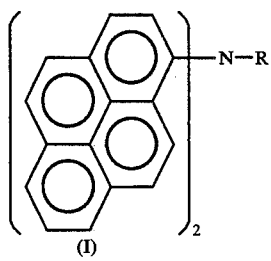

wherein X represents a halogen such as bromine or iodine; R is the same as defined in the formula (I).

The dipyrenylamine derivative of the formula (I) can also be prepared by allowing di(1-pyrenyl)amine having formula (IIIb) to react with a halide having formula (IVa):

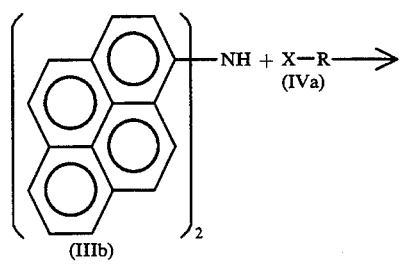

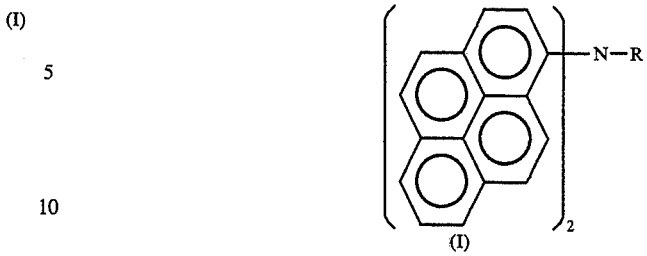

wherein X and R are respectively the same as defined in the formula (IV) and the formula (I).

When R represents an aryl group in the above-mentioned formulas (I), (IIIa) and (IVa), examples of the aryl group include a non-fused aromatic hydrocarbon group, a fused polycyclic hydrocarbon group and a heterocyclic aromatic hydrocarbon group.

Specific examples of the non-fused aromatic hydrocarbon group are phenyl group, biphenyl group and terphenyl group.

Specific examples of the fused polycyclic hydrocarbon group are pentalenyl group, indenyl group, naphthyl group, azulenyl group, heptalenyl group, biphenylenyl group, as-indacenyl group, fluorenyl group, S-indacenyl group, acenaphthylenyl group, pleiadenyl group, acenaphthenyl group, phenalenyl group, phenanthryl group, anthryl group, fluoranthenyl group, acephenanthrylenyl group, aceanthrylenyl group, triphenylenyl group, pyrenyl group, chrysenyl group and naphthacenyl group.

Specific examples of the heterocyclic aromatic hydrocarbon group are thienyl group, furyl group, 2-pyridyl group, 4-pyridyl group, 3-indolyl group, 2-quinolinyl group, 3,4-benzpyranyl group, acridinyl group, thiazolyl group, benzothiazolonyl group, 9-methylcarbazolyl group, 9-ethylcarbazolyl group, 9-propylcarbazolyl group, 9-phenylcarbazolyl group, 9-tolylcarbazolyl group and 4-pyrazolyl group.

Examples of the substituent of the aryl group represented by R in the formula (I) are as follows:

(1) Halogen, cyano group and nitro group.

(2) An alkyl group having 1 to 12 carbon atoms, more preferably an alkyl group having 1 to 8 carbon atoms, and further preferably an alkyl group having 1 to 4 carbon atoms, which may have a substituent.

Specific examples of the above alkyl group include methyl group, ethyl group, n-propyl group, i-propyl group, t-butyl group, s-butyl group, n-butyl group, i-butyl group, 2-hydroxyethyl group, 2-cyanoethyl group, 2-ethoxyethyl group, 2-methoxyethyl group, benzyl group, 4-chlorobenzyl group, 4-methylbenzyl group, 4-methoxybenzyl group and 4-phenylbenzyl group.

Specific examples of the substituent of the above alkyl group are hydroxyl group, cyano group, alkoxyl group having 1 to 4 carbon atoms, phenyl group, halogen, phenyl group substituted with alkyl group having 1 to 4 carbon atoms, and phenyl group substituted with alkoxyl group having 1 to 4 carbon atoms.

(3) An alkoxyl group represented by $-OR^1$, in which $R^1$ represents the same alkyl group which may have a substituent as defined in (2).

Specific examples of the above alkoxyl group include methoxy group, ethoxy group, n-propoxy group, i-propoxy group, t-butoxy group, n-butoxy group, s- butoxy group, i-butoxy group, 2-hydroxyethoxy group, 2-cyanoethoxy group, benzyloxy group and 4-methylbenzyloxy group.

(4) An aryloxy group, in which an aryl group represents, for example, a phenyl group and a naphthyl group. The above aryloxy group may have a substituent such as an alkoxyl group having 1 to 4 carbon atoms, an alkyl group having 1 to 4 carbon atoms or a halogen.

Specific examples of the above aryloxy group include phenoxy group, 1-naphthyloxy group, 2-naphthyloxy group, 4-methylphenoxy group, 4-methoxyphenoxy group, 4-chlorophenoxy group and 6-methyl-2-naphthyloxy group.

(5) An alkylmercapto group represented by —SR$^1$, in which R$^1$ represents the same alkyl group which may have a substituent as defined in (2).

Specific examples of the above alkylmercapto group include methylthio group, ethylthio group, phenylthio group and p-methylphenylthio group.

(6)

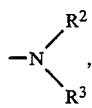

in which R$^2$ and R$^3$ independently represent hydrogen, the same alkyl group which may have a substituent as defined in (2) or an aryl group which may have a substituent. As the aryl group, phenyl group, biphenyl group or naphthyl group can be employed, which may have a substituent such as an alkoxyl group having 1 to 4 carbon atoms, an alkyl group having 1 to 4 carbon atoms or a halogen. R$^2$ R$^3$ may form a ring in combination or in combination with carbon atoms on the aryl group.

Specific examples of the above

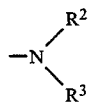

include an amino group, diethylamino group, N-methyl-N-phenylamino group, N,N-diphenylamino group, N,N-di(p-tolyl)amino group, dibenzylamino group, piperidino group, morpholino group and julolidyl group.

(7) An alkylenedioxy group such as methylenedioxy group, or an alkylenedithio group such as methylenedithio group.

When R represents an alkyl group in the previously mentioned formulas (I), (IIIa) and (IVa), the same alkyl group which may have a substituent as defined in (2) of the specific examples of the substituent of the aryl group can be employed.

Specific examples of the dipyrenylamine derivatives according to the present invention are shown in the following Table 1:

TABLE 1

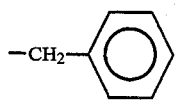

| Compound No. | R |
|---|---|
| 1 | —CH$_3$ |
| 2 | —CH$_2$CH$_3$ |
| 3 | 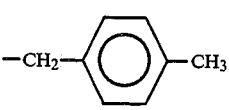 |
| 4 | 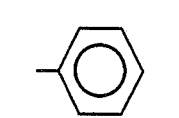 |
| 5 |  |
| 6 | 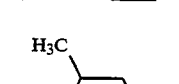 |
| 7 |  |
| 8 |  |
| 9 | 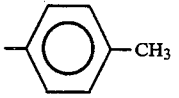 |
| 10 | 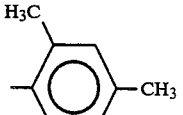 |
| 11 |  |

TABLE 1-continued $$\left(\underset{\text{[perylene]}}{\bigcirc}-N-R\right)_2$$

| Compound No. | R |
|---|---|
| 12 | 4-ethylphenyl |
| 13 | 3-ethylphenyl |
| 14 | 4-tert-butylphenyl |
| 15 | 4-methoxyphenyl |
| 16 | 3-methoxyphenyl |
| 17 | 2-methoxyphenyl |
| 18 | 2-methoxy-5-methylphenyl |
| 19 | 4-ethoxyphenyl |
| 20 | 2,5-dimethoxyphenyl |
| 21 | 1-naphthyl |
| 22 | 4-methyl-1-naphthyl |
| 23 | 2-anthryl |
| 24 | 1-pyrenyl |
| 25 | 5-methyl-2-thienyl |
| 26 | 4-(N,N-dimethylamino)phenyl |
| 27 | 4-chlorophenyl |

TABLE 1-continued

[Structure: dipyrenylamine with N—R, subscript 2]

| Compound No. | R |
|---|---|
| 28 | —C₆H₄—CN (para-cyanophenyl) |
| 29 | N-ethylcarbazol-yl group (with C₂H₅ on N) |

Among the above-mentioned dipyrenylamine derivatives, the following dipyrenylamine derivatives having formula (II) are novel compounds:

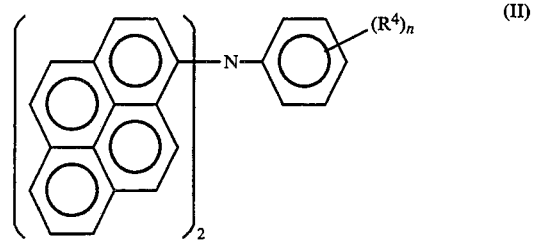

(II)

wherein R⁴ represents hydrogen, an alkyl group having 1 to 12 carbon atoms, which may have a substituent, an alkoxyl group represented by —OR¹, in which R¹ represents an alkyl group having 1 to 12 carbon atoms, which may have a substituent, a phenyl group which may have a substituent, or a halogen; n is an integer of 1 to 5; and when n is 2 to 5, R⁴ may be the same or different.

The dipyrenylamine derivative having the above formula (II) can be prepared by allowing an aniline derivative having formula (III) to react with a halogenopyrene having formula (IV):

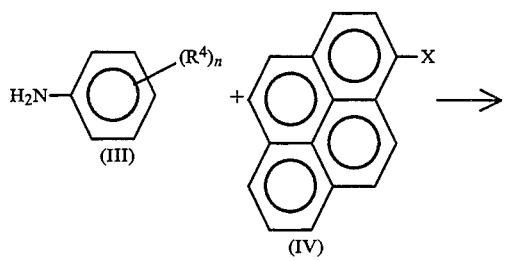

(III)  (IV)

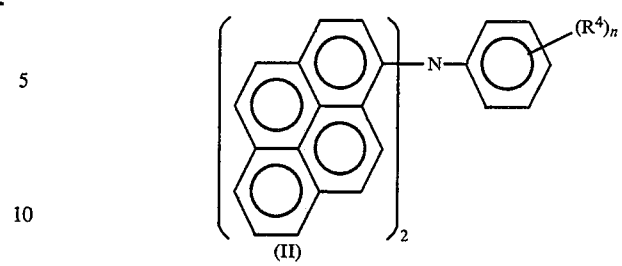

(II)

wherein R⁴ and n are the same as defined in the formula (II); and X represents a halogen.

The dipyrenylamine derivative of the formula (II) can also be prepared by allowing a N-phenyl-1-aminopyrene derivative having formula (V) to react with a halogenopyrene having formula (IV):

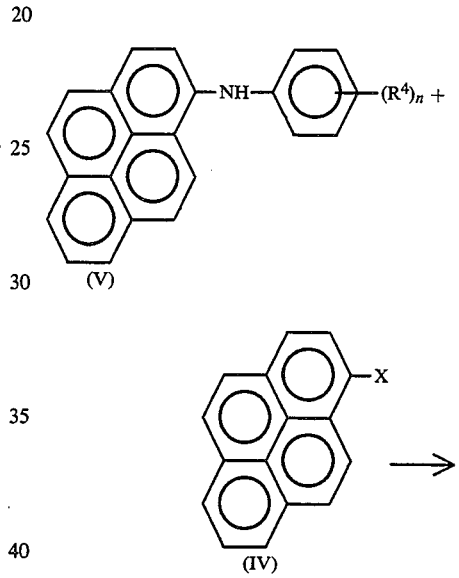

(V)

(IV)

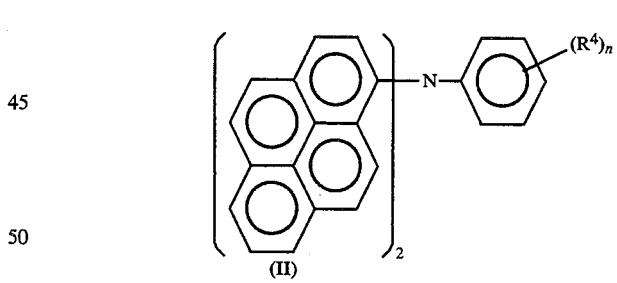

(II)

wherein R⁴ and n are the same as previously defined in the formula (II); and X represents a halogen.

Examples of the alkyl group which may have a substituent, the alkoxyl group which may have a substituent, and the phenyl group which may have a substituent represented by R⁴ in the formulas (II), (III) and (V) are substantially the same as the specific examples of the corresponding substituents of the aryl group represented by R in the formula (I).

More specifically, the alkyl group represented by R⁴ is a lower alkyl group such as methyl group, ethyl group, propyl group and butyl group.

Specific examples of the alkoxyl group represented by R⁴ include a lower alkoxyl group such as methoxy group, ethoxy group and propoxy group.

The above-mentioned alkyl group and alkoxyl group may have a substituent such as phenyl group, a halogen, alkoxyl group and aryloxy group.

The phenyl group represented by $R^4$ in the formulas (II), (III) and (V) also may have a substituent such as a lower alkyl group, for instance, methyl group, ethyl group, propyl group and butyl group; a lower alkoxyl group, for instance, methoxy group, ethoxy group and propoxy group; and a halogen, for instance, bromine, chlorine and fluorine.

Specific examples of the halogen represented by X in the formula (IV) are bromine and iodine.

The dipyrenylamine derivatives of the present invention having formula (II) can be prepared by allowing the previously mentioned aniline derivative having formula (III) to react with the halogenopyrene having formula (IV), or the N-phenyl-1-aminopyrene derivative having formula (V) to react with the halogenopyrene having formula (IV), in a solvent in a stream of nitrogen at about 150° to 250° C. in the presence of copper powder, copper oxide or copper halogenide, with an alkaline salt added thereto in a sufficient amount for neutralizing hydrogen halogenide generated in the course of the reaction. In this case, the solvent may not be used in the reaction.

Examples of the above-mentioned alkaline salt used in the reaction are sodium hydroxide, potassium hydroxide, sodium carbonate and potassium carbonate. Examples of the solvent used in the reaction are nitrobenzene, dichlorobenzene, quinoline, N,N-dimethylformamide, dimethyl sulfoxide, N-methylpyrrolidone and 1,3-dimethyl-2-imidazolidinone.

The above-mentioned novel dipyrenylamine derivatives of the present invention, which are remarkably effective as photoconductive materials in the electrophotographic photoconductor, are optically or chemically sensitized with a sensitizer such as a dye or Lewis acid. In addition, the dipyrenylamine derivatives effectively function as a charge transporting material in a function-separating type electrophotographic photoconductor where an organic or inorganic pigment serves as a charge generating material.

In the photoconductors according to the present invention, at least one dipyrenylamine derivative of the formula (I) is contained in the photoconductive layers 2, 2a, 2b, 2c and 2d. The dipyrenylamine derivatives can be employed in different ways, for example, as shown in FIGS. 4 to 8.

Figure 4:
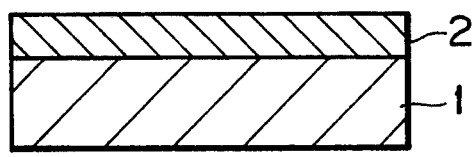
FIG. 4 is a schematic cross-sectional view of a first example of an electrophotographic photoconductor according to the present invention.

In the photoconductor as shown in FIG. 4, a photoconductive layer 2 is formed on an electroconductive substrate 1, which photoconductive layer 2 comprises a dipyrenylamine derivative, a sensitizing dye and a binder agent (binder resin). In this photoconductor, the dipyrenylamine derivative works as a photoconductive material, through which charge carriers which are necessary for the light decay of the photoconductor are generated and transported. However, the dipyrenylamine derivative itself scarcely absorbs light in the visible light range and, therefore, it is necessary to add a sensitizing dye which absorbs light in the visible light range in order to form latent electrostatic images by use of visible light.

Figure 5:
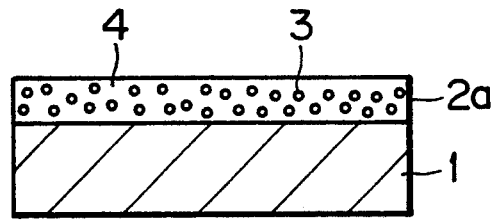
FIG. 5 is a schematic cross-sectional view of a second example of an electrophotographic photoconductor according to the present invention.

Referring to FIG. 5, there is shown a cross-sectional view of another embodiment of an electrophotographic photoconductor according to the present invention. In the figure, on the electroconductive substrate 1, there is formed a photoconductive layer 2a comprising a charge generating material 3 dispersed in a charge transporting medium 4 comprising a dipyrenylamine derivative and a binder agent. In this embodiment, the dipyrenylamine derivative and the binder agent (or a mixture of the binder agent and a plasticizer) in combination constitute the charge transporting medium 4. The charge generating material 3, which is, for example, an inorganic or organic pigment, generates charge carriers. The charge transporting medium 4 accepts the charge carriers generated by the charge generating material 3 and transports those charge carriers.

In this electrophotographic photoconductor, it is essential that the light-absorption wavelength regions of the charge generating material 3 and the dipyrenylamine derivative not overlap in the visible light range. This is because, in order to have the charge generating material 3 produce charge carriers efficiently, it is necessary to allow the light to reach the surface of the charge generating material 3. The dipyrenylamine derivatives of formula (I) scarcely absorb the light in the visible range. Therefore, especially when combined with the charge generating material 3 which absorbs the light in the visible region and generates charge carriers, the dipyrenylamine derivatives of the present invention can work effectively as charge transporting materials.

Figure 6:
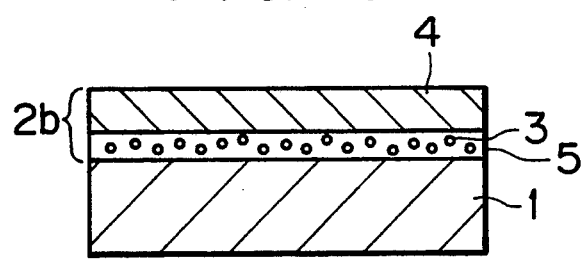
FIG. 6 is a schematic cross-sectional view of a third example of an electrophotographic photoconductor according to the present invention.

Referring to FIG. 6, there is shown a cross-sectional view of a further embodiment of an electrophotographic photoconductor according to the present invention. In the figure, there is formed on an electroconductive substrate 1 a two-layered photoconductive layer 2b comprising a charge generation layer 5 containing the charge generating material 3, and a charge transport layer 4 containing a dipyrenylamine derivative of formula (I).

In this photoconductor, the light which has passed through the charge transport layer 4 reaches the charge generation layer 5, where charge carriers are generated. The charge carriers which are necessary for the light decay for latent electrostatic image formation are generated by the charge generating material 3, and accepted and transported by the charge transport layer 4. In the charge transport layer 4, the dipyrenylamine derivative mainly works for transportation of charge carriers. The generation and transportation of the charge carriers are performed by the same mechanism as that in the photoconductor shown in FIG. 5.

Figure 7:
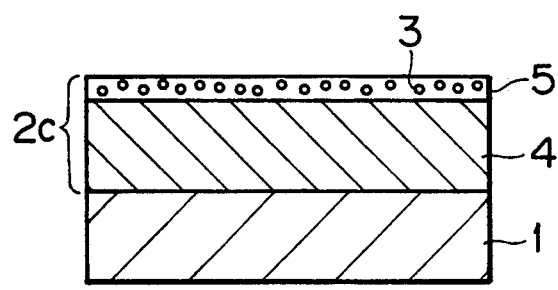
FIG. 7 is a schematic cross-sectional view of a fourth example of an electrophotographic photoconductor according to the present invention.

Referring to FIG. 7, there is shown still another embodiment of an electrophotographic photoconductor according to the present invention. In the figure, the overlaying order of the charge generation layer 5 and the charge transport layer 4 is reversed. The mechanism of the generation and transportation of charge carriers is substantially the same as that of the photoconductor shown in FIG. 6.

Figure 8:
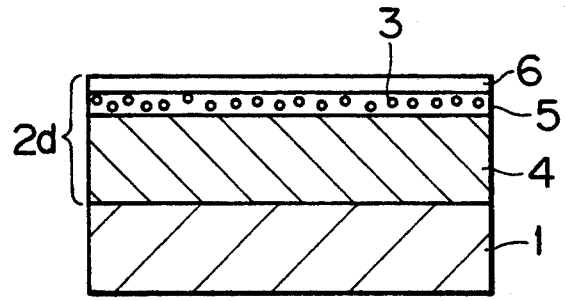
FIG. 8 is a schematic cross-sectional view of a fifth example of an electrophotographic photoconductor according to the present invention.

In the above photoconductor, a protective layer 6 may be formed on the charge generation layer 5 as shown in FIG. 8 for improving the mechanical strength thereof.

When the electrophotographic photoconductor according to the present invention as shown in FIG. 4 is prepared, at least one dipyrenylamine derivative of formula (I) is dispersed in a binder resin solution, and a sensitizing dye is then added to the mixture, so that a photoconductive layer coating liquid is prepared. The thus prepared photoconductive layer coating liquid is coated on an electroconductive substrate i and dried, so that a photoconductive layer 2 is formed on the electroconductive substrate 1.

It is preferable that the thickness of the photoconductive layer 2 be in the range of 3 to 50 μm, more preferably in the range of 5 to 20 μm. It is preferable that the amount of the dipyrenylamine derivative contained in the photoconductive layer 2 be in the range of 30 to 70 wt. %, more preferably about 50 wt. %.

It is preferable that the amount of the sensitizing dye contained in the photoconductive layer 2 be in the range of 0.1 to 5 wt. %, more preferably in the range of 0.5 to 3 wt. %.

Specific examples of the sensitizing dye for use in the present invention are: triarylmethane dyes such as Brilliant Green, Victoria Blue B, Methyl Violet, Crystal Violet and Acid Violet 6B; xanthene dyes such as Rhodamine B, Rhodamine 6G, Rhodamine G Extra, Eosin S, Erythrosin, Rose Bengale and Fluoresceine; thiazine dyes such as Methylene Blue; cyanine dyes such as cyanin; and pyrylium dyes such as 2,6-diphenyl-4-(N,N-dimethylaminophenyl)thiapyrylium perchlorate and benzopyrylium salts (described in Japanese Patent Publication 48-25658). These sensitizing dyes can be used alone or in combination.

The electrophotographic photoconductor shown in FIG. 5 can be obtained by dispersing finely-divided particles of the charge generating material 3 in the solution in which at least one dipyrenylamine derivative for use in the present invention and the binder agent are dissolved, coating the above-prepared dispersion on the electroconductive substrate 1 and then drying the same to form the photoconductive layer 2a.

It is preferable that the thickness of the photoconductive layer 2a be in the range of 3 to 50 μm, more preferably in the range of 5 to 20 μm. It is preferable that the amount of the dipyrenylamine derivative contained in the photoconductive layer 2a be in the range of 10 to 95 wt. %, more preferably in the range of 30 to 90 wt. %.

It is preferable that the amount of the charge generating material 3 contained in the photoconductive layer 2a be in the range of 0.1 to 50 wt. %, more preferably in the range of 1 to 20 wt. %.

Specific examples of the charge generating material 3 are as follows: inorganic pigments such as selenium, selenium-tellurium, cadmium sulfide, cadmium sulfide-selenium and α-silicone; and organic pigments, such as C.I. Pigment Blue 25 (C.I. 21180), C.I. Pigment Red 41 (C.I. 21200), C.I. Acid Red 52 (C.I. 45100), and C.I. Basic Red 3 (C.I. 45210); an azo pigment having a carbazole skeleton (Japanese Laid-Open Patent Application 53-95033), an azo pigment having a distyryl benzene skeleton (Japanese Laid-Open Patent Application 53-133445), an azo pigment having a triphenylamine skeleton (Japanese Laid-Open Patent Application 53-132347), an azo pigment having a dibenzothiophene skeleton (Japanese Laid-Open Patent Application 54-21728), an azo pigment having an oxadiazole skeleton (Japanese Laid-Open Patent Application 54-12742), an azo pigment having a fluorenone skeleton (Japanese Laid-Open Patent Application 54-22834), an azo pigment having a bisstilbene skeleton (Japanese Laid-Open Patent Application 54-17733), an azo pigment having a distyryl oxadiazole skeleton (Japanese Laid-Open Patent Application 54-2129), and an azo pigment having a distyryl carbazole skeleton (Japanese Laid-Open Patent Application 54-14967); a phthalocyanine pigment such as C.I. Pigment Blue 16 (C.I. 74100); indigo pigments such as C.I. Vat Brown 5 (C.I. 73410) and C.I. Vat Dye (C.I. 73030); and perylene pigments such as Algol Scarlet B (made by Bayer Co., Ltd.) and Indanthrene Scarlet R (made by Bayer Co., Ltd.). These charge generating materials may be used alone or in combination.

The electrophotographic photoconductor shown in FIG. 6 can be obtained as follows:

The charge generating material is vacuum-deposited on the electroconductive substrate 1, or the dispersion in which finely-divided particles of the charge generating material 3 are dispersed in an appropriate solvent, together with the binder agent when necessary, is coated on the electroconductive substrate 1 and dried, so that the charge generation layer 5 is formed. When necessary, the charge generation layer 5 is subjected to surface treatment by buffing and adjustment of the thickness thereof. On the thus formed charge generation layer 5, a coating liquid in which at least one dipyrenylamine derivative and the binder agent are dissolved is coated and dried, so that the charge transport layer 4 is formed. In the charge generation layer 5, the same charge generating material as employed in the previously mentioned photoconductive layer 2a can be used.

The thickness of the charge generation layer 5 is 5 μm or less, more preferably 2 μm or less. It is preferable that the thickness of the charge transport layer 4 be in the range of 3 to 50 μm, more preferably in the range of 5 to 20 μm. When the charge generation layer 5 is obtained by coating the dispersion in which finely-divided particles of the charge generating material 3 are dispersed in the binder agent, it is preferable that the amount of finely-divided particles of the charge generating material 3 contained in the charge generation layer 5 be in the range of 10 to 95 wt. %, more preferably in the range of about 50 to 90 wt. %. It is preferable that the amount of the dipyrenylamine derivative contained in the charge transport layer 4 be in the range of 10 to 95 wt. %, more preferably in the range of 30 to 90 wt. %.

The electrophotographic photoconductor shown in FIG. 7 can be obtained as follows:

A coating liquid in which the dipyrenylamine derivative and the binder agent are dissolved is coated on the electroconductive substrate 1 and dried to form the charge transport layer 4. On the thus formed charge transport layer 4, a dispersion prepared by dispersing finely-divided particles of the charge generating material 3 in the solvent, in which the binder agent is dissolved when necessary, is coated by spray coating and dried to form the charge generation layer 5 on the charge transport layer 4. The respective formulations of the charge generation layer and the charge transport layer are the same as previously described in FIG. 6.

The electrophotographic photoconductor shown in FIG. 8 can be obtained by forming a protective layer 6 on the charge generation layer 5 obtained in FIG. 7 by spray-coating an appropriate resin solution. As a resin to be employed in the protective layer 6, any binder agents to be described later can be used.

Specific examples of materials for the electroconductive substrate 1 of the electrophotographic photoconductor according to the present invention include a metallic plate or foil made of aluminum, a plastic film on which a metal such as aluminum is deposited, and a sheet of paper which has been treated so as to be electroconductive.

Specific examples of the binder agent for use in the present invention are condensation resins such as polyamide, polyurethane, polyester, epoxy resin, polyketone and polycarbonate; and vinyl copolymers such as polyvinylketone, polystyrene, poly-N-vinylcarbazole and polyacrylamide. All the resins having insulating properties and adhesive properties can be employed.

Some plasticizers may be added to the above-mentioned binder agent, when necessary. Examples of such plasticizers are halogenated paraffin, polybiphenyl chloride, dimethylnaphthalene and dibutyl phthalate.

Furthermore, in the electrophotographic photoconductors according to the present invention, an adhesive layer or a barrier layer can be interposed between the electroconductive substrate and the photoconductive layer when necessary. Examples of the material for use in the adhesive layer or the barrier layer are polyamide, nitrocellulose and aluminum oxide. It is preferable that the thickness of the adhesive layer or the barrier layer be 1 μm or less.

When copying is performed by use of the photoconductors according to the present invention, the surface of the photoconductor is charged uniformly in the dark to a predetermined polarity. The uniformly charged photoconductor is exposed to a light image so that a latent electrostatic image is formed on the photoconductor. The thus formed latent electrostatic image is developed by a developer to a visible image, and when necessary, the developed image can be transferred to a sheet of paper. The electrophotographic photoconductors according to the present invention have the advantages in that the photosensitivity is high and the flexibility is improved.

Other features of this invention will become apparent in the course of the following description of exemplary embodiments, which are given for illustration of the invention and are not intended to be limiting thereof.

Preparation Example 1

[Synthesis of N,N-di(1-pyrenyl)-p-toluidine (Compound No. 9 in Table 1)]

A mixture of 1.07 g (10.0 mmol) of p-toluidine, 6.56 g (20.0 mmol) of 1-iodopyrene, 5.53 g of potassium carbonate, 0.64 g of copper powder, and 50 ml of nitrobenzene was subjected to azeotropic dehydration in a stream of nitrogen, using an ester tube, with stirring, at 207° C. for 6.5 hours.

After the mixture was cooled to room temperature, the resulting insoluble material of the mixture was removed by filtration by use of Celite. The thus obtained filtrate was concentrated under the reduced pressure, and nitrobenzene was removed therefrom.

Chloroform was added to the above obtained residue. The chloroform layer was washed with water and dried with magnesium sulfide. The thus obtained extract was further concentrated under the reduced pressure, so that an oily dark brown material was obtained.

This oily material was subjected to column chromatography using silica gel as a carrier and a mixed solvent of toluene and n-hexane (1:2) as an eluting solution. The product was recrystallized from a mixed solvent of ethanol and dimethylformamide, so that 1.33 g of N,N-di(1-pyrenyl)-p-toluidine (Compound No. 9) was obtained as yellow plate crystals with a 26.2% yield. The above compound melted at 272.5°–273.5° C.

The results of the elemental analysis of the compound were as follows:

|  | % C | % H | % N |
| --- | --- | --- | --- |
| Calculated | 92.28 | 4.96 | 2.76 |
| Found | 92.10 | 4.81 | 2.99 |

The above calculation was based on the formula for N,N-di (1-pyrenyl) -p-toluidine of $C_{39}H_{25}N$.

FIG. 1 shows an infrared spectrum of N,N-di(1-pyrenyl) -p-toluidine taken by use of a KBr tablet.

Preparation Example 2

[Synthesis of N,N-di(1-pyrenyl)-p-anisidine (Compound No. 15 in Table 1)]

The procedure for preparing N,N-di(1-pyrenyl)-p-toluidine in Preparation Example 1 was repeated except that 10.0 mmol of p-toluidine employed in Preparation Example 1 was replaced by 10.0 mmol of p-anisidine, so that N,N-di(1-pyrenyl)-p-anisidine of the present invention was obtained.

The above obtained compound melted at 245.5°–246.5° C.

The results of the elemental analysis of the compound were as follows:

|  | % C | % H | % N |
| --- | --- | --- | --- |
| Calculated | 89.46 | 4.81 | 2.68 |
| Found | 89.67 | 4.54 | 2.58 |

Figure 2:
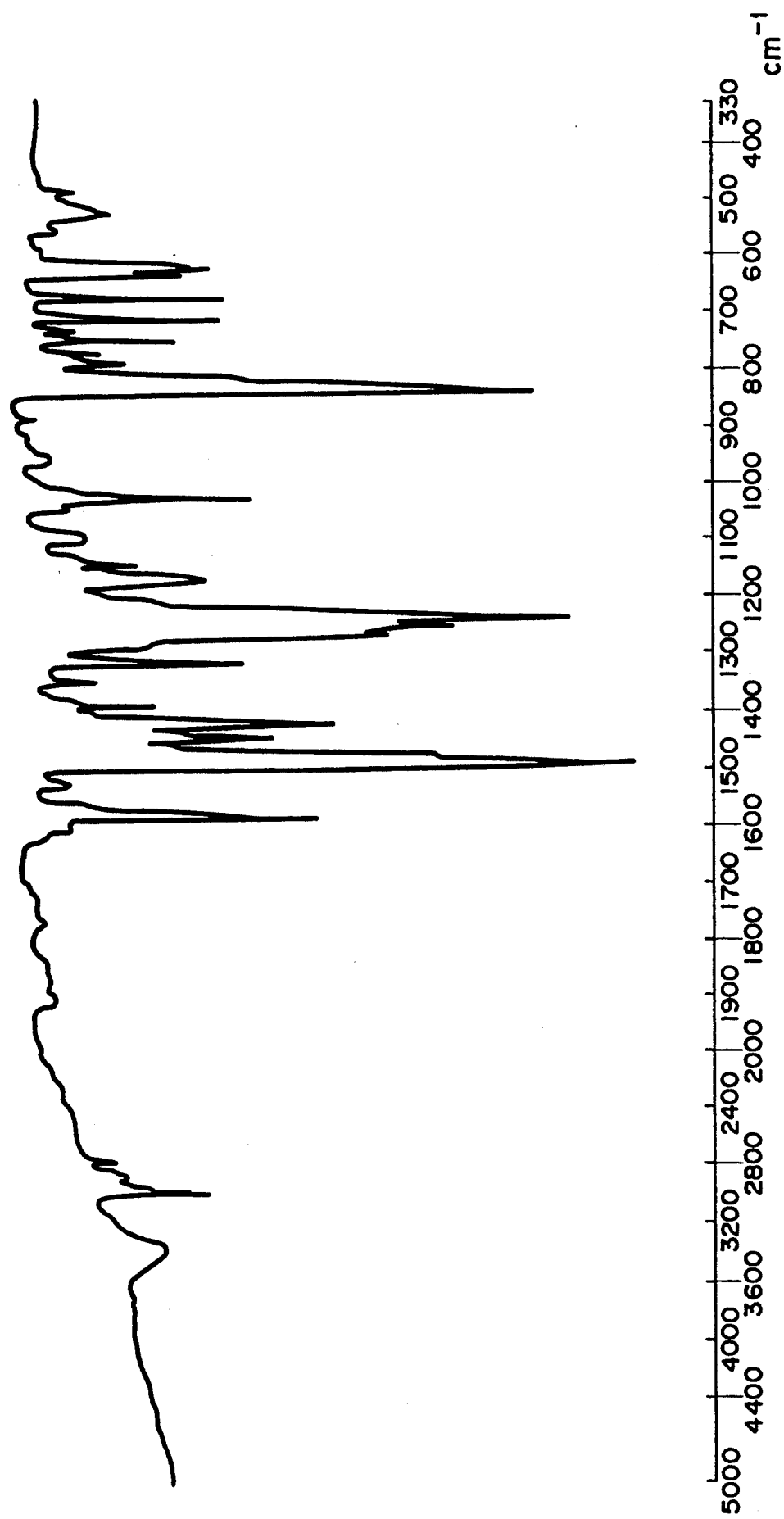
FIG. 2 is an IR spectrum of a dipyrenylamine derivative obtained in Preparation Example 2.

FIG. 2 shows an infrared spectrum of the above compound taken by use of a KBr tablet.

Preparation Example 3

[Synthesis of N,N-di(1-pyrenyl)aniline (Compound No. 5 in Table 1)]

A mixture of 0.55 g (1.9 mmol) of N-phenyl-1-aminopyrene, 0.92 g (2.8 mmol) of 1-iodopyrene, 0.52 g of potassium carbonate, 0.12 g of copper powder, and 15 ml of nitrobenzene was subjected to azeotropic dehydration in a stream of nitrogen, using an ester tube, with stirring, at 207° C. for 6 hours.

After the mixture was cooled to room temperature, the resulting insoluble material of the mixture was removed by filtration by use of Celite. The thus obtained filtrate was concentrated under the reduced pressure, and nitrobenzene was removed therefrom.

The above obtained residue was successively washed with methanol, water, and methanol, so that 0.89 g (96%) of dark green crude crystals was obtained. The thus obtained crystals were recrystallized from N,N-dimethylformamide, so that 0.46 g of N,N-di(1-pyrenyl)aniline (Compound No. 5) was obtained as yellow crystals with a 49% yield. The above compound melted at 280° C. or more.

The results of the elemental analysis of the compound were as follows:

|  | % C | % H | % N |
| --- | --- | --- | --- |
| Calculated | 92.47 | 4.70 | 2.83 |
| Found | 92.53 | 4.59 | 2.77 |

The above calculation was based on the formula for N,N-di (1-pyrenyl)aniline of $C_{38}H_{23}N$.

Figure 3:
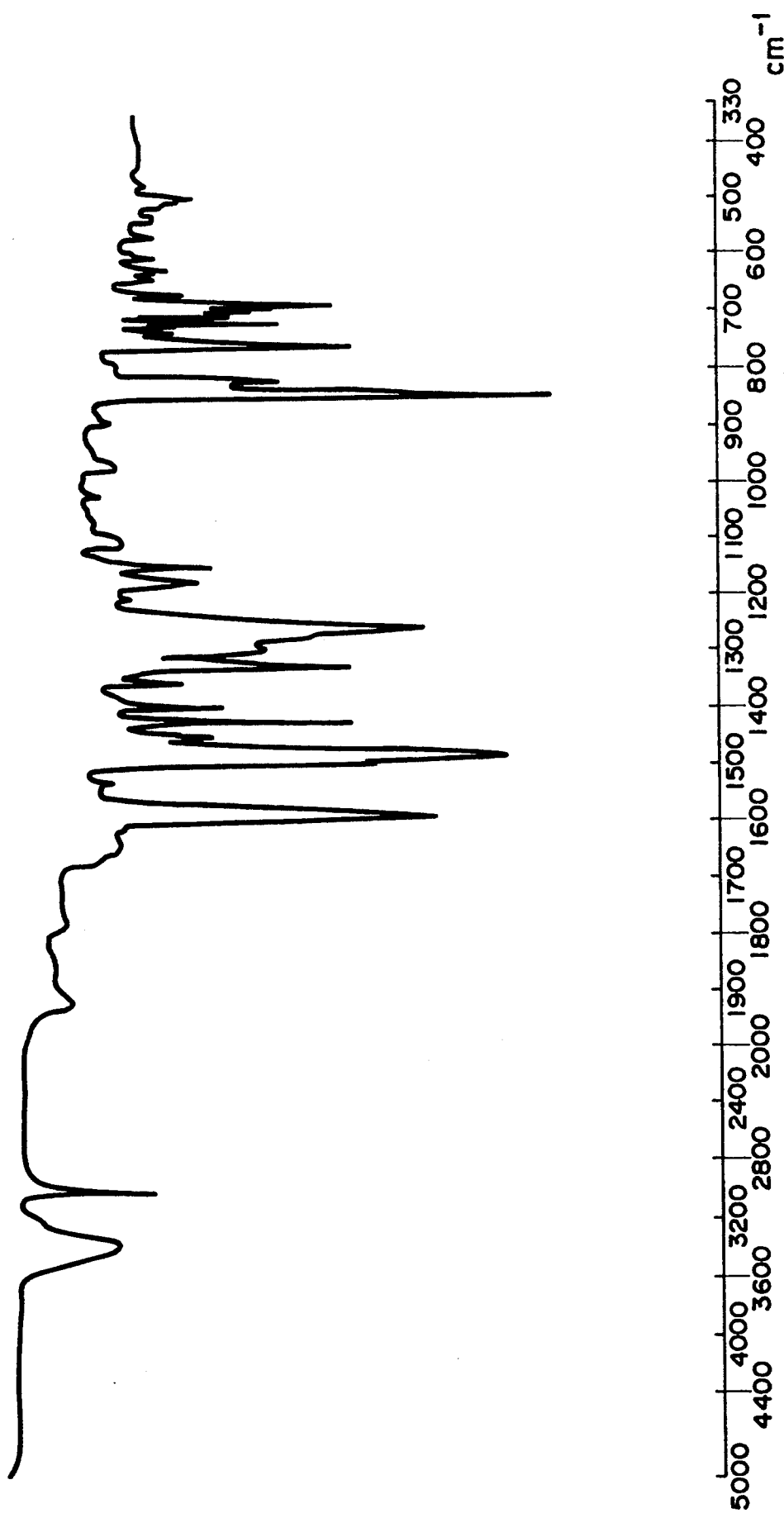
FIG. 3 is an IR spectrum of a dipyrenylamine derivative obtained in Preparation Example 3.

FIG. 3 shows an infrared spectrum of N,N-di(1-pyrenyl)-aniline taken by use of a KBr tablet.

EXAMPLE 1

76 parts by weight of Diane Blue (C.I. Pigment Blue 25: C.I. 21180) serving as a charge generating material, 1260 parts by weight of a 2% tetrahydrofuran solution of a polyester resin (Trademark "Vylon 200" made by Toyobo Company, Ltd.) and 3700 parts by weight of tetrahydrofuran were dispersed and ground in a ball mill. The thus prepared dispersion was coated on an aluminum surface of an aluminum-deposited polyester film serving as an electroconductive substrate by a doctor blade, and dried at room temperature, so that a charge generation layer with a thickness of about 1 μm was formed on the electroconductive substrate.

2 parts by weight of N,N-di(1-pyrenyl)-p-toluidine (Compound No. 9 in Table 1) prepared in Preparation Example 1 serving as a charge transporting material, 2 parts by weight of polycarbonate resin (Trademark "Panlite K-1300" made by Teijin Limited.) and 16 parts by weight of tetrahydrofuran were mixed to prepare a coating liquid for a charge transport layer. This liquid was coated on the above formed charge generation layer by a doctor blade, and dried at 80° C. for 2 minutes and then at 120° C. for 5 minutes, so that a charge transport layer with a thickness of about 20 μm was formed on the charge generation layer. Thus an electrophotographic photoconductor No. 1 according to the present invention was prepared.

EXAMPLES 2 to 33

The procedure for preparation of the electrophotographic photoconductor No. 1 in Example 1 was repeated except that Diane Blue serving as a charge generating material for use in the charge generation layer and N,N-di -(1-pyrenyl)-p-toluidine (Compound No. 9) serving as a charge transporting material for use in the charge transport layer in Example 1 were respectively replaced by each of the charge generating materials and charge transporting materials listed in the following Table 2, whereby electrophotographic photoconductors No. 2 to No. 33 according to the present invention were prepared.

TABLE 2

| Photoconductor | Charge Generating Material | Charge Transporting Material (Dipyrenylamine Derivative No.) |
|---|---|---|
| 1 | (structure) | 9 |
| 2 | (structure) | 9 |
| 3 | (structure) (hereinafter referred to as P-1) | 9 |

TABLE 2-continued
| Photoconductor | Charge Generating Material | Charge Transporting Material (Dipyrenylamine Derivative No.) |
|---|---|---|
| 4 | 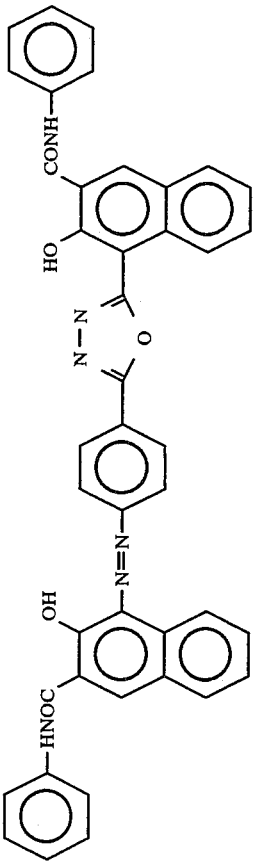 | 9 |
| 5 | 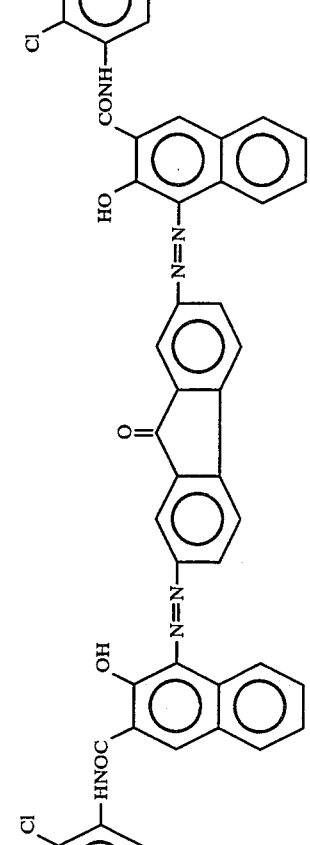 (hereinafter referred to as P-2) | 9 |
| 6 | 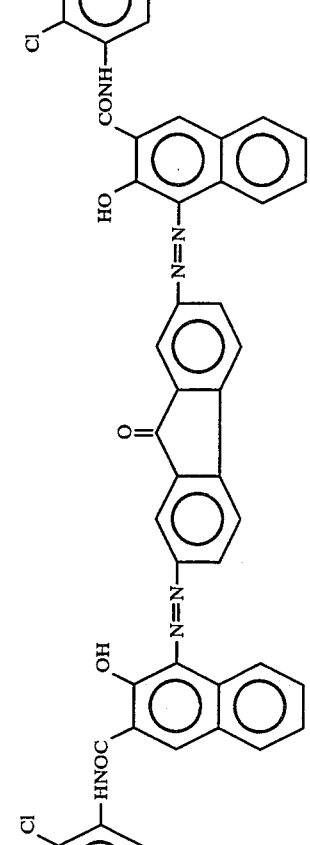 (hereinafter referred to as P-3) | 9 |
| 7 | β-type Copper Phthalocyanine | 9 |

TABLE 2-continued

| Photoconductor | Charge Generating Material | Charge Transporting Material (Dipyrenylamine Derivative No.) |
|---|---|---|
| 8 | [structure: bis-azo compound with OCH₃/H₃CO substituents, naphthol CONH-phenyl groups] | 15 |
| 9 | [structure: bis-azo compound with Cl substituents, naphthol CONH-phenyl groups] | 15 |
| 10 | P-1 | 15 |
| 11 | P-2 | 15 |
| 12 | P-3 | 15 |
| 13 | P-1 | 3 |
| 14 | P-2 | 3 |
| 15 | P-3 | 3 |
| 16 | P-1 | 6 |
| 17 | P-2 | 6 |
| 18 | P-3 | 6 |
| 19 | P-1 | 12 |
| 20 | P-2 | 12 |
| 21 | P-3 | 12 |
| 22 | P-1 | 5 |
| 23 | P-2 | 5 |
| 24 | P-3 | 5 |
| 25 | P-1 | 20 |
| 26 | P-2 | 20 |
| 27 | P-3 | 20 |
| 28 | P-1 | 21 |
| 29 | P-2 | 21 |
| 30 | P-3 | 21 |
| 31 | P-1 | 27 |
| 32 | P-2 | 27 |
| 33 | P-3 | 27 |

EXAMPLE 34

Selenium was vacuum-deposited on an aluminum plate with a thickness of about 300 μm, so that a charge generation layer with a thickness of about 1 μm was formed on the aluminum plate.

2 parts by weight of N,N-di(1-pyrenyl)-p-toluidine (Compound No. 9), 3 parts by weight of polyester resin (Trademark "Polyester Adhesive 49000" made by Du Pont de Nemours, E. I. & Co.) and 45 parts by weight of tetrahydrofuran were mixed to prepare a coating liquid for a charge transport layer. This liquid was coated on the above formed charge generation layer by a doctor blade, and dried at room temperature and then under the reduced pressure, so that a charge transport layer with a thickness of about 10 μm was formed on the charge generation layer Thus an electrophotographic photoconductor No. 34 according to the present invention was prepared.

EXAMPLE 35

The procedure for preparing the electrophotographic photoconductor No. 34 in Example 34 was repeated except that a charge generation layer with a thickness of about 0.6 μm was formed on the same aluminum plate as employed in Example 34 by deposition of the following perylene pigment instead of selenium, so that an electrophotographic photoconductor No. 35 according to the present invention was prepared:

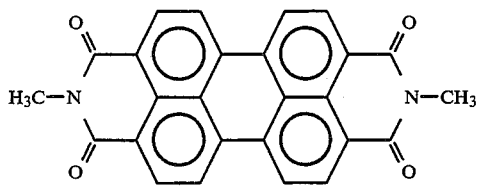

EXAMPLE 36

1 part by weight of the same Diane Blue as employed in Example 1 and 158 parts by weight of tetrahydrofuran were mixed and ground in a ball mill to prepare a dispersion. To the thus prepared dispersion, 12 parts by weight of N,N-di(1-pyrenyl)-p-toluidine (Compound No. 9) prepared in Preparation Example 1 and 18 parts by weight of polyester resin (Trademark "Polyester Adhesive 49000" made by Du Pont de Nemours, E. I. & Co.) were added to prepare a coating liquid for a photoconductive layer. This liquid was coated on an aluminum-deposited polyester film serving as an electroconductive substrate by a doctor blade, and dried at 100° C. for 30 minutes, so that a photoconductive layer with a thickness of about 16 μm was formed on the electroconductive substrate. Thus, an electrophotographic photoconductor No. 36 according to the present invention was prepared.

EXAMPLE 37

2 parts by weight of N,N-di(1-pyrenyl)-p-toluidine (Compound No. 9) serving as a charge transporting material, 2 parts by weight of polycarbonate resin (Trademark "Panlite K-1300" made by Teijin Limited.) and 16 parts by weight of tetrahydrofuran were mixed to prepare a coating liquid for a charge transport layer. This liquid was coated on an aluminum-deposited polyester film serving as an electroconductive substrate by a doctor blade, and dried at 80° C. for 2 minutes and then at 120° C. for 5 minutes, so that a charge transport layer with a thickness of about 20 μm was formed on the electroconductive substrate.

13.5 parts by weight of bisazo pigment (P-2), 5.4 parts by weight of polyvinyl butyral (Trademark "XYHL" made by Union Carbide Japan K.K.), 680 parts by weight of tetrahydrofuran and 1020 parts by weight of ethyl cellosolve were mixed and ground in a ball mill to prepare a dispersion. To this dispersion, 1700 parts by weight of additional ethyl cellosolve were added and stirred to prepare a coating liquid for a charge generation layer. This liquid was coated on the above formed charge transport layer by spray coating and dried at 100° C. for 10 minutes, so that a charge generation layer with a thickness of about 0.2 μm was formed on the charge transport layer.

A methanol/n-butanol solution of a polyamide resin (Trademark "CM-8000" made by Toray Industries, Inc.) was coated on the above formed charge generation layer by spray coating and dried at 120° C. for 30 minutes, so that a protective layer with a thickness of about 0.5 μm was formed on the charge generation layer. Thus, an electrophotographic photoconductor No. 37 according to the present invention was prepared.

Each of the thus prepared electrophotographic photoconductors No. 1 to No. 37 according to the present invention was charged under application of −6 kV or +6 kV of corona charge for 20 seconds, using a commercially available electrostatic copying sheet testing apparatus ("Paper Analyzer Model SP-428" made by Kawaguchi Electro Works Co., Ltd.). Then, each electrophotographic photoconductor was allowed to stand in the dark for 20 seconds without applying any charge thereto, and the surface potential Vpo (V) of the photoconductor was measured. Each photoconductor was then illuminated by a tungsten lamp in such a manner that the illuminance on the illuminated surface of the photoconductor was 4.5 lux, and the exposure $E_{\frac{1}{2}}$ (lux.-sec) required to reduce the initial surface potential Vpo (V) to ½ thereof was measured. The results are shown in Table 3.

Furthermore, each of the electrophotographic photoconductors No. 1 to No. 37 according to the present invention was charged by use of a commercially available electrophotographic copying machine. Then a latent electrostatic image was formed on the photoconductor using an original by illuminating the charged photoconductor. The thus formed latent electrostatic image was developed by a dry-type developer to a visible image. The thus obtained toner image was electrostatically transferred to a sheet of normal paper, so that a clear transferred image was obtained. A clear image was also obtained when a wet-type developer was employed for development of the latent electrostatic image.

TABLE 3

| Photoconductor No | Vpo (V) | $E_{\frac{1}{2}}$ (lux · sec) |
| --- | --- | --- |
| 1 | −1446 | 1.51 |
| 2 | −1451 | 1.67 |
| 3 | −1422 | 1.01 |
| 4 | −1387 | 1.17 |
| 5 | −1321 | 0.80 |
| 6 | −1015 | 0.52 |
| 7 | −951 | 1.50 |
| 8 | −1406 | 1.17 |
| 9 | −1488 | 1.23 |
| 10 | −1305 | 0.90 |
| 11 | −1297 | 0.76 |

TABLE 3-continued

| Photoconductor No | Vpo (V) | E½ (lux · sec) |
|---|---|---|
| 12 | −921 | 0.46 |
| 13 | −1521 | 1.30 |
| 14 | −1451 | 1.22 |
| 15 | −1389 | 1.01 |
| 16 | −1351 | 0.96 |
| 17 | −1259 | 0.78 |
| 18 | −1002 | 0.53 |
| 19 | −1361 | 1.04 |
| 20 | −1231 | 0.96 |
| 21 | −966 | 0.60 |
| 22 | −1421 | 1.10 |
| 23 | −1381 | 0.97 |
| 24 | −997 | 0.70 |
| 25 | −1301 | 0.96 |
| 26 | −127 | 0.79 |
| 27 | −896 | 0.49 |
| 28 | −1483 | 1.15 |
| 29 | −1421 | 1.01 |
| 30 | −1056 | 0.77 |
| 31 | −1522 | 1.30 |
| 32 | −1379 | 1.38 |
| 33 | −1092 | 1.22 |
| 34 | −1721 | 1.56 |
| 35 | −1166 | 2.41 |
| 36 | +1251 | 1.62 |
| 37 | +1065 | 0.92 |

The electrophotographic photoconductors of the present invention can provide the improved resistance to heat and mechanical shocks as well as the photoconductive properties thereof. Furthermore, the photoconductors according to the present invention can be manufactured at low cost.

What is claimed is:

1. An electrophotographic photoconductor comprising an electroconductive substrate and a photoconductive layer formed thereon, said photoconductive layer comprising a sensitizer dye and a dipyrenylamine derivative of formula (I):

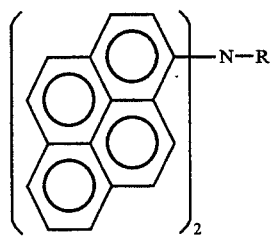

(I)

wherein R is selected from the group consisting of an alkyl group with 1 to 12 carbon atoms, an aryl group and a heterocyclic aromatic hydrocarbon group, each of which may have a substituent.

2. The electrophotographic photoconductor as claimed in claim 1, wherein said alkyl group represented by R is selected form the group consisting of methyl group, ethyl group, n-propyl group, i-propyl group, t-butyl group, s-butyl group, n-butyl group, i-butyl group, 2-hydroxyethyl group, 2-cyanoethyl group, 2-ethoxyethyl group, 2-methoxyethyl group, benzyl group, 4-chlorobenzyl group, 4-methylbenzyl group, 4-methoxybenyl group and 4-phenylbenzyl group.

3. The electrophotographic photoconductor as claimed in claim 1, wherein said substituent of said alkyl group represented by R is selected from the group consisting of hydroxyl group, cyano group, alkoxyl group having 1 to 4 carbon atoms, phenyl group, halogen, a phenyl group substituted with an alkyl group having 1 to 4 carbon atoms, and a phenyl group substituted with an alkoxyl group having 1 to 4 carbon atoms.

4. The electrophotographic photoconductor as claimed in claim 1, wherein said aryl group represented by R is a non-fused aromatic hydrocarbon group.

5. The electrophotographic photoconductor as claimed in claim 4, wherein said non-fused aromatic hydrocarbon group represented by R is selected from the group consisting of phenyl group, biphenyl group and terphenyl group, which may have a substituent.

6. The electrophotographic photoconductor as claimed in claim 1, wherein said aryl group represented by R is a fused polycyclic hydrocarbon group.

7. The electrophotographic photoconductor as claimed in claim 6, wherein said fused polycyclic hydrocarbon group is selected from the group consisting of a pentalenyl group, indenyl group, naphthyl group, azulenyl group, heptalenyl group, biphenylenyl group, as-indacenyl group, fluorenyl group, S-indacenyl group, acenaphthylenyl group, pleiadenyl group, acenaphthenyl group, phenalenyl group, phenanthryl group, anthryl group, fluoranthenyl group, acephenanthrylenyl group, aceanthrylenyl group, triphenylenyl group, pyrenyl group, chrysenyl group and naphthacenyl group.

8. The electrophotographic photoconductor as claimed in claim 1, wherein said aryl group represented by R is a heterocyclic aromatic hydrocarbon group.

9. The electrophotographic photoconductor as claimed in claim 8, wherein said heterocyclic aromatic hydrocarbon group is selected from the group consisting of thienyl group, furyl group, 2-pyridyl group, 4-pyridyl group, 3-indolyl group, 2-quinolinyl group, 3,4-benzpyranyl group, acridinyl group, thiazolyl group, benzothiazolonyl group, 9-methylcarbazolyl group, 9-ethylcarbazolyl group, 9-propylcarbazolyl group, 9-phenylcarbazolyl group, 9-tolylcarbazolyl group and 4-pyrazolyl group.

10. The electrophotographic photoconductor as claimed in claim 1, wherein said substituent of said aryl group represented by R is selected from the group consisting of halogen, cyano group and nitro group.

11. The electrophotographic photoconductor as claimed in claim 1, wherein said substituent of said aryl group represented by R is an alkyl group having 1 to 12 carbon atoms, which may have a substituent.

12. The electrophotographic photoconductor as claimed in claim 11, wherein said substituent of said alkyl group represented by $R^1$ is selected from the group consisting of hydroxyl group, cyano group, an alkoxyl group having 1 to 4 carbon atoms, phenyl group, halogen, a phenyl group substituted with an alkyl group having 1 to 4 carbon atoms, and a phenyl group substituted with an alkoxyl group having 1 to 4 carbon atoms.

13. The electrophotographic photoconductor as claimed in claim 11, wherein said alkyl group having 1 to 12 carbon atoms, which may have a substituent, is selected from the group consisting of methyl group, ethyl group, n-propyl group, i-propyl group, t-butyl group, s-butyl group, n-butyl group, i-butyl group, 2-hydroxyethyl group, 2-cyanoethyl group, 2-ethoxyethyl group, 2-methoxyethyl group, benzyl group, 4-chlorobenzyl group, 4-methylbenzyl group, 4-methoxy -benzyl group and 4-phenylbenzyl group.

14. The electrophotographic photoconductor as claimed in claim 1, wherein said substituent of said aryl group represented by R is an alkoxyl group represented by —OR¹ in which R¹ represents an alkyl group having 1 to 12 carbon atoms, which may have a substituent.

15. The electrophotographic photoconductor as claimed in claim 14, wherein said substituent of said alkyl group represented by R¹ is selected from the group consisting of hydroxyl group, cyano group, an alkoxyl group having 1 to 4 carbon atoms, phenyl group, halogen, a phenyl group substituted with an alkyl group having 1 to 4 carbon atoms, and a phenyl group substituted with an alkoxyl group having 1 to 4 carbon atoms.

16. The electrophotographic photoconductor as claimed in claim 14, wherein said alkoxyl group represented by —OR¹ is selected from the group consisting of methoxy group, ethoxy group, n-propoxy group, i-propoxy group, t-butoxy group, n-butoxy group, s-butoxy group, i-butoxy group, 2-hydroxyethoxy group, 2-cyanoethoxy group, benzyloxy group and 4-methylbenzyloxy group.

17. The electrophotographic photoconductor as claimed in claim 1, wherein said substituent of said aryl group represented by R is an aryloxy group which may have a substituent.

18. The electrophotographic photoconductor as claimed in claim 17, wherein said aryloxy group is selected from the group consisting of phenoxy group and naphthyloxy group.

19. The electrophotographic photoconductor as claimed in claim 17, wherein said substituent of said aryloxy group is selected from the group consisting of an alkoxyl group having 1 to 4 carbon atoms, an alkyl group having 1 to 4 carbon atoms, and a halogen.

20. The electrophotographic photoconductor as claimed in claim 17, wherein said aryloxy group which may have a substituent is selected from the group consisting of a phenoxy group, 1-naphthyloxy group, 2-naphthyloxy group, 4-methylphenoxy group, 4-methoxyphenoxy group, 4-chlorophenoxy group and 6-methyl-2-naphthyloxy group.

21. The electrophotographic photoconductor as claimed in claim 1, wherein said substituent of said aryl group represented by R is an alkylmercapto group represented by —SR¹ in which R¹ represents an alkyl group having 1 to 12 carbon atoms, which may have a substituent.

22. The electrophotographic photoconductor as claimed in claim 21, wherein said substituent of said alkyl group represented by R¹ is selected from the group consisting of hydroxyl group, cyano group, an alkoxyl group having 1 to 4 carbon atoms, phenyl group, halogen, a phenyl group substituted with an alkyl group having 1 to 4 carbon atoms, and a phenyl group substituted with an alkoxyl group having 1 to 4 carbon atoms.

23. The electrophotographic photoconductor as claimed in claim 21, wherein said alkylmercapto group represented by —SR¹ is selected from the group consisting of methylthio group, ethylthio group, phenylthio group and p-methylphenylthio group.

24. The electrophotographic photoconductor as claimed in claim 1, wherein said substituent of said aryl group represented by R is a group of the formula

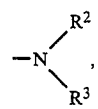

in which $R^2$ and $R^3$ independently are selected from the group consisting of hydrogen,
an alkyl group having 1 to 12 carbon atoms, an aryl group, said alkyl and aryl group may have a substituent, and $R^2$ and $R^3$, in combination, forming a ring.

25. The electrophotographic photoconductor as claimed in claim 24, wherein said substituent of said alkyl group represented by $R^2$ or $R^3$ is selected from the group consisting of hydroxyl group, cyano group, an alkoxyl group having 1 to 4 carbon atoms, phenyl group, halogen, a phenyl group substituted with an alkyl group having 1 to 4 carbon atoms, and a phenyl group substituted with an alkoxyl group having 1 to 4 carbon atoms.

26. The electrophotographic photoconductor as claimed in claim 24, wherein said aryl group represented by $R^2$ or $R^3$ is selected from the group consisting of phenyl group, biphenyl group and naphthyl group.

27. The electrophotographic photoconductor as claimed in claim 24, wherein the substituent of said aryl group represented by $R^2$ or $R^3$ is selected from the group consisting of an alkoxyl group having 1 to 4 carbon atoms, an alkyl group having 1 to 4 carbon atoms and a halogen.

28. The electrophotographic photoconductor as claimed in claim 24 wherein said group represented by

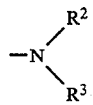

is selected from the group consisting of an amino group, diethylamino group, N-methyl-N-phenylamino group, N,N-diphenylamino group, N,N-di(p-tolyl)amino group, dibenzylamino group, piperidino group, morpholino group and julolidyl group.

29. The electrophotographic photoconductor as claimed in claim 1, wherein said substituent of said aryl group represented by R is selected from the group consisting cf an alkylenedioxy group and an alkylenedithio group.

30. The electrophotographic photoconductor as claimed in claim 29, wherein said alkylenedioxy group is methylenedioxy group.

31. The electrophotographic photoconductor as claimed in claim 29, wherein said alkylenedithio group is methylenedithio group.

32. The electrophotographic photoconductor as claimed in claim 6, wherein said phenyl group with a substituent represented by R is a group represented by

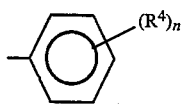

wherein $R^4$ is selected from the group consisting of hydrogen, an alkyl group having 1 to 12 carbon atoms, which may have a substituent, an alkoxyl group represented by $-OR^1$, in which $R^1$ represents an alkyl group having 1 to 12 carbon atoms, which may have a substituent, a phenyl group which may have a substituent, or a halogen, n is an integer of 1 to 5, and when n is 2 to 5, $R^4$ may be the same or different.

33. The electrophotographic photoconductor as claimed in claim 32, wherein said alkyl group represented by $R^4$ has 1 to 8 carbon atoms and said alkyl group represented by $R^1$ has 1 to 8 carbon atoms.

34. The electrophotographic photoconductor as claimed in claim 33, wherein said alkyl group represented by $R^4$ has 1 to 4 carbon atoms and said alkyl group represented by $R^1$ has 1 to 4 carbon atoms.

35. The electrophotographic photoconductor as claimed in claim 32, wherein said substituent of said alkyl group represented by $R^4$ is selected from the group consisting of hydroxyl group, cyano group, alkoxyl group having 1 to 4 carbon atoms, phenyl group, a halogen, a phenyl group substituted with an alkyl group having 1 to 4 carbon atoms, and a phenyl group substituted with an alkoxyl group having 1 to 4 carbon atoms.

36. The electrophotographic photoconductor as claimed in claim 32, wherein said substituent of said phenyl group represented by $R^4$ is selected from the group consisting of an alkyl group having 1 to 4 carbon atoms, a phenyl group substituted with an alkoxyl group having 1 to 4 carbon atoms, and a halogen.

37. The electrophotographic photoconductor as claimed in claim 1, wherein said dipyrenylamine derivative is in an amount ranging from 30 wt. % to 70 wt. % of the entire weight of said photoconductive layer.

38. The electrophotographic photoconductor as claimed in claim 1, wherein said photoconductive layer further comprises a sensitizer dye and a binder agent, and has a thickness of 3 μm to 50 μm.

39. The electrophotographic photoconductor as claimed in claim 1, wherein said photoconductive layer comprises a charge generating material dispersed in a charge transporting medium which comprises said dipyrenylamine derivative and a binder agent.

40. The electrophotographic photoconductor as claimed in claim 39, wherein the amount of said dipyrenylamine derivative is in the range of 10 wt. % to 90 wt. % of the entire weight of said photoconductive layer, and the amount of said charge generating material is in the range of 0.1 wt. % to 50 wt. % of the entire weight of said photoconductive layer.

41. The electrophotographic photoconductor as claimed in claim 1, wherein said photoconductive layer comprises a charge generation layer containing a charge generating material, and a charge transfer layer containing said dipyrenylamine derivative as a charge transporting material.

42. The electrophotographic photoconductor as claimed in claim 41, wherein the amount of said charge generating layer is in the range of 10 wt. % to 95 wt. % of the entire weight of said charge generation layer, and the amount of said dipyrenylamine derivative is in the amount of 10 wt. % to 95 wt. % of the entire weight of said charge transport layer.

* * * * *

UNITED STATES PATENT AND TRADEMARK OFFICE
CERTIFICATE OF CORRECTION

PATENT NO. : 5,356,742

DATED : October 18, 1994

INVENTOR(S) : Shimada et al.

It is certified that error appears in the above-identified patent and that said Letters Patent is hereby corrected as shown below:

Column 7, line 40, "$R^2R^3$" should read --$R^2$ and $R^3$--.

Column 7, line 41 after "combination" insert --,--.

Column 14, line 66, after "electroconductive substrate" insert --1-- and delete "i".

Column 23, Figure 4, substitute the following figure:

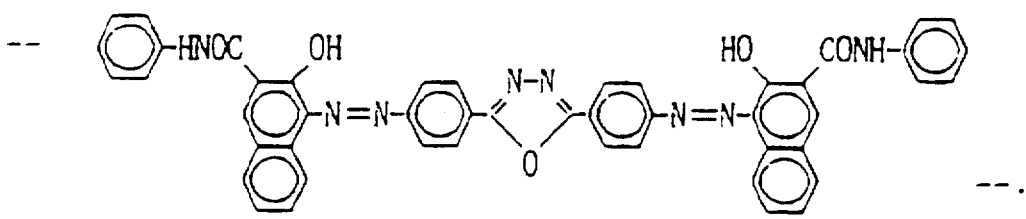

Column 27, line 7 "N,N-di(1-pyrenyl)" should read --N,N-di(1-pyrenyl)--.

Column 27, line 17 after "generation layer" insert --.--.

UNITED STATES PATENT AND TRADEMARK OFFICE
CERTIFICATE OF CORRECTION

PATENT NO. : 5,356,742

DATED : October 18, 1994

INVENTOR(S) : Shimada et al.

It is certified that error appears in the above-identified patent and that said Letters Patent is hereby corrected as shown below:

Column 29, line 15, "-127" should read ---1278--.

Column 31, line 47, after "by -SR$^1$" insert --;--.

Signed and Sealed this

Sixteenth Day of January, 1996

BRUCE LEHMAN

Attest:

Attesting Officer

Commissioner of Patents and Trademarks